(12) United States Patent
Miller

(10) Patent No.: US 6,422,465 B2
(45) Date of Patent: *Jul. 23, 2002

(54) BAR CODE GASOLINE BLENDING

(75) Inventor: Charles B. Miller, Ashland, KY (US)

(73) Assignee: Marathon Ashland Petroleum LLC, Findlay, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/728,287

(22) Filed: Dec. 1, 2000

Related U.S. Application Data

(63) Continuation of application No. 07/708,585, filed on May 31, 1991, now Pat. No. 6,163,738.

(51) Int. Cl.[7] .................................................. G07B 15/02
(52) U.S. Cl. ........................................ 235/384; 141/94
(58) Field of Search ............................... 235/381, 384, 235/435, 375, 376, 462.01; 141/94, 98, 231; 705/412, 413; 700/213, 239, 240, 241

(56) References Cited

U.S. PATENT DOCUMENTS

| | | | | |
|---|---|---|---|---|
| 4,263,945 A | * | 4/1981 | Van Ness | ..................... 141/98 |
| 4,345,146 A | * | 8/1982 | Story et al. | .................. 235/381 |
| 4,469,149 A | * | 9/1984 | Walkey et al. | ................ 141/94 |
| 4,479,807 A | | 10/1984 | Rebandt | |
| 4,615,362 A | | 10/1986 | Hartman | |
| 4,821,697 A | | 4/1989 | McDougal | |
| 4,876,653 A | | 10/1989 | McSpadden | |
| 4,951,720 A | | 8/1990 | Grantham | |
| 4,963,745 A | | 10/1990 | Maggard | |
| 4,974,552 A | | 12/1990 | Sickafus | |
| 4,978,029 A | * | 12/1990 | Furrow et al. | .................. 222/1 |
| 5,018,645 A | * | 5/1991 | Zinsmeyer | .................. 222/14 |
| 5,029,100 A | | 7/1991 | Young et al. | |
| 5,163,586 A | | 11/1992 | Zinsmeyer | |
| 6,112,981 A | | 9/2000 | McCall | |
| 6,163,738 A | * | 12/2000 | Miller | ........................ 700/239 |

FOREIGN PATENT DOCUMENTS

| | | | |
|---|---|---|---|
| JP | 63-212127 | * | 9/1988 |
| JP | 01-279099 A | * | 11/1989 |
| JP | 11-20630 | * | 1/1999 |

* cited by examiner

*Primary Examiner*—Michael G. Lee
*Assistant Examiner*—Diane I. Lee
(74) *Attorney, Agent, or Firm*—Richard D. Stone; James F. Porcello, Jr.

(57) ABSTRACT

A process and apparatus for preparation of custom blended fuels is disclosed. A bar code on a fuel tank or vehicle, such as an automobile, is scanned by a bar code reader operatively associated with a fuel dispensing means to convey information about a fuel required or desired to a computer controlled customized blender associated with the fuel dispensing means. Multiple fuel components, such as gasoline and replenishable fuel components such as methanol and ethanol may be custom mixed at the point of purchase. Preferably an octane analyzer and other fuel property analyzers, such as RVP analyzers, are associated with individual component or blended gasoline streams.

5 Claims, 1 Drawing Sheet

BAR CODE GASOLINE BLENDING

CROSS REFERENCE TO RELATED APPLICATIONS

This application is a continuation of prior co-pending application U.S. Ser. No. 07/708,585, Point of Purchase Gasoline Analyzing Blending, Miller, C. B., May 31, 1991, now U.S. Pat. No. 6,163,738 which is incorporated by reference.

BACKGROUND OF THE INVENTION

I. Field of the Invention

The present invention relates to the analysis and blending of motor vehicle fuels.

II. Description of the Prior Art

The problem of tailoring motor vehicle fuels, especially gasoline octane, to the needs of various consumer vehicles has long been apparent. Solutions have included providing a number of different gasoline pumps at a single retail outlet so that the consumer may select the pump which dispenses the fuel best suited to a vehicle's requirements and blending pumps which blend a high octane component such as alkylate with a low octane gasoline according to an octane dialed into the dispensing pump. Recently, this situation has been complicated by mandated gasoline formulations as dictated by Congress and various states, and by different tax treatments granted to ethanol, methanol, and other replenishable fuel components in different states. Also, legislation in specifying maximum Reid vapor pressure (RVP) in various locals has become popular and must be balanced against the need for some minimum RVP in order to ensure starting of the motor vehicle in cold weather and cold climates. Taken altogether these motorist demands and government regulations can best be satisfied by blending gasoline from more than two components and by blending as close to the point of sale as possible.

Recent advances in octane determination include U.S. Pat. No. 4,800,279 to Hieftje et.al.; U.S. Pat. No. 4,963,745 to S. M. Maggard; J. J. Kelley et.al., 61 Analytical Chemistry 313–320, Feb. 15, 1989; and European Patent Office document 285,251 of October 1988. Reid vapor pressure can be analyzed intermittently or continuously by Reid Monitor No. 44770 by Precision Scientific Inc., Chicago.

BRIEF SUMMARY OF THE INVENTION

Accordingly, the present invention provides an apparatus for blending and dispensing customized fuel to a vehicle in response to a bar code on the vehicle comprising multiple fuel component storage means connective with individual conduit means, a mixing means, for blending said fuel, fluidly connective with said storage means, and producing a blended or customized fuel, at least one analyzing means operatively associated with at least one individual fuel component, said mixing means or said blended fuel, a fuel dispensing means comprising a bar code reader fluidly connective with said mixing means, a bar code on said vehicle, one or more computer means, receiving inputs from said bar code reader on said fuel dispensing means, for determining the fuel requirements of said vehicle based upon said bar code on said vehicle and for controlling the blending of fuel to produce said blended fuel required by, or specified for, said vehicle based upon said bar code on said vehicle and a display means displaying at least one of cost, volume or properties of said customized fuel delivered to said vehicle in response to said bar code on said vehicle.

In another embodiment, the present invention provides a process for blending and dispensing a customized fuel to a vehicle in response to a bar code on the vehicle comprising maintaining multiple fuel component storage means connective with individual conduit means and metering means, reading a bar code on said vehicle and using one or more computer means, receiving inputs from said bar code reader, to determine the fuel requirements of said vehicle, blending a fuel for said vehicle by mixing in a mixing means connective with said fuel component storage means to produce a blended fuel, dispensing said customized fuel into said vehicle, displaying at least one of cost, volume, or properties of said customized fuel dispensed to said vehicle in response to said bar code on said vehicle.

In preferred embodiments, two, preferably three or more gasoline (or other fuel) blending components are delivered to a point adjacent to the point of sale to the motorist and are blended by an apparatus which proportions the flow of individual components in response to signals indicative of the gasoline quality variables, octane, Reid vapor pressure, percent alcohol, etc. The preferred octane for control purposes is motor octane, but pump octane or research octane or any combination of these three may be utilized. Analysis of octane is preferably performed by near-infrared spectroscopy, more preferably NIR operating in the t-butyl/methyne band, and most preferably through a signal which comprises the second derivative of the absorbance in that particular band. Preferred methods of control are proportioning pumps operating in response to an octane or other variable, optional additional input by the consumer, and periodically or continuously reset according to feedback received from the octane measured in the blended fuel. Reid vapor pressure and other gasoline variables are controlled similarly. Setting of the variable speed proportioning pumps in response to information input by the vehicle via bar-code reading, input by the consumer, processing of the NIR absorbance signal, and other quality control-indicative signals for feedback to the proportioning pumps, pricing and calculation of total cost are all well within the state of the art of computer technology.

While the invention will be particularly preferred for use in gasoline dispensing pumps, it may be used for other fuels such as control of cetane in diesel fuel, nitrobenzene, and other alcohol fuels used for automobile racing and even liquified petroleum gases such as blending butane and propane for fuel and heating purposes.

BRIEF DESCRIPTION OF THE DRAWING

The FIGURE shows schematically a preferred embodiment of the invention including principal components multiple fuel component storage means 20, individual conduit means 30, metering means 40, pump activating means 50, analyzing means 60, computer means 70, computer input means 80, computer display means 90, and fuel dispensing means 100.

DETAILED DESCRIPTION

Apparatus

Figure 1:
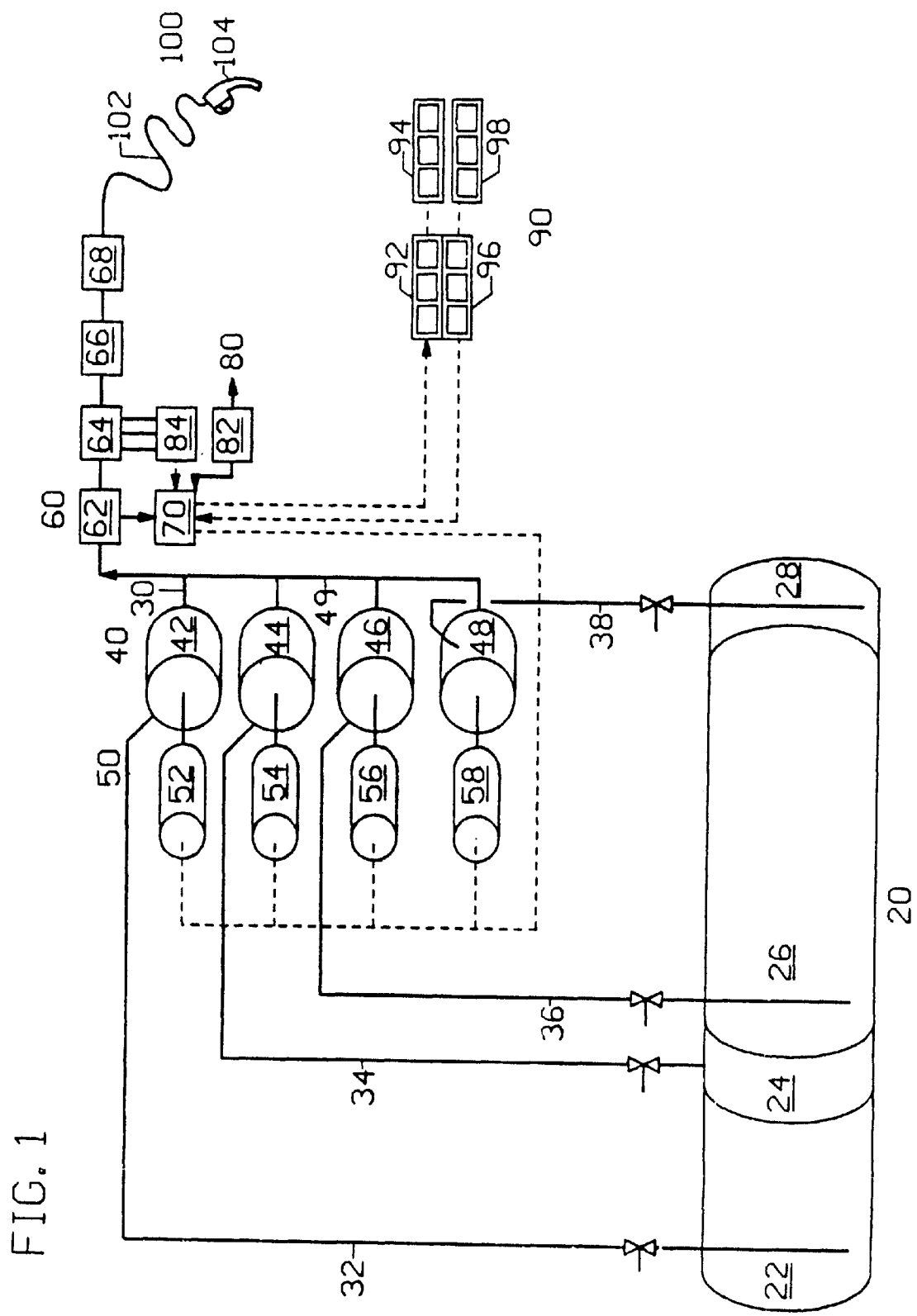

The apparatus for use with the present invention is not narrowly critical and will be generally obtainable from commercial sources. Preferred devices for use with each of the principle components of the invention are:

Multiple fuel component storage means 20: The multiple fuel component storage means 20 can be any suitable, multiple storage means for receiving and dispensing the individual fuel components and may be located underground (with suitable leak retention means), above ground or transportable as in a tank truck. Reinforced fiberglass is particularly preferred, but steel and other plastics can be used so long as they are proof against the components being contained. The compartments may be pressurized, e.g. with nitrogen to aid withdrawal. While the particularly preferred embodiment having multiple compartments within a single tank is shown in the FIGURE, separate tanks may, of course, be employed for each component.

Individual conduit means 30: The individual conduit means 30 can be copper or suitable plastic tubing and should be equipped with hand valves, reverse-flow check valves, and suitable inlets for receiving the components; tank truck, rail car, barge, or other transport devices which may itself be compartmented so as to carry a number of different blending components.

Metering means 40: The metering means 40 are preferably positive displacement pumps, e.g., gear pumps, piston pumps, peristaltic pumps, sliding vane pumps, or other positive displacement pumps which dispense a predetermined amount of volume with each stroke or rotation. The pumps may be variable- displacement themselves, but will be preferably driven by pump activating means 50 which can be adjusted to deliver more or less of each component per second during dispensing.

Analyzing Means 60: The analyzing means 60 preferably comprises a near-infrared (NIR) analyzer operating in the range preferred in U.S. Pat. No. 4,963,745 to S. M. Maggard. A Reid vapor pressure analyzer, preferably an ASTM—approved analyzer, and an alcohol analyzer, preferably an NIR or GC may be used. Multiple analyzers adapted for analyzing individual components or desired physical properties of the fuel may be provided.

Computer means 70: The computer means 70 is a computer and preferably will take the second derivative of the absorbance in the preferred band. The computer should also be capable of receiving price and octane inputs and resetting itself to provide the desired octane, calculate the final price, gallons, and other desired variables such as cash or credit, etc.

Computer input means 80: The computer input means 80 can comprise a dial, a series of push buttons, a conventional telephone keypad, for inputting the price, the octane, charge or credit card, etc. The computer will also receive input from a bar code reader and a bar code on the vehicle.

Computer display means 90: The computer display means 90 can be any sort of Blinn tube, liquid-crystal display, cathode-ray tube or other form of register for displaying the preset octane, price, volume delivered, and total sale plus Reid vapor pressure or any other parameters desired to be displayed.

Fuel dispensing means 100: The fuel dispensing means 100 comprises a conventional, flexible hose, nozzle and dispensing valve, all available from gasoline retail outlet equipment suppliers. The nozzle may be keyed to deliver only when set to the fuel required by the vehicle, e.g. by a bar-code on the gas tank coupled with a bar-code reader on the nozzle.

DESCRIPTION OF THE PREFERRED EMBODIMENTS

Referring to the FIGURE, the multiple fuel component storage means 20 are connected to individual metering means 40 through individual conduit means 30 which are driven by their respective pump activating means 50 and respond to signals received from computer means 70 which in turn receives signals from analyzing means 60 and sends outputs to computer display means 90 and to pump activating means 50. The fuel is dispensed through fuel dispensing means 100.

In operation, regular gasoline flows from regular gasoline compartment 22 through individual conduit means 32 and is metered by gasoline pump 42 through NIR Analyzer 62, Reid vapor pressure analyzer 64, alcohol analyzer 66, and meter 68, and the blended fuel is dispensed through hose 102 and nozzle and dispensing valve 104. Alkylate flows similarly from alkylate compartment 24 through its own individual system as does Reid vapor pressure component flow from Reid vapor pressure compartment 26 and ethanol from ethanol compartment 28.

The components are blended in mixer 49 which preferably employs a powered mixer for thorough blending. The NIR Analyzer 62 and the Reid vapor pressure analyzer 64 send signals to the computer which, in turn, outputs signals to change the speed of gasoline metering motor 52, alkylate metering motor 54, and ethanol metering motor 58, at short intervals. The computer also varies the speed of Reid vapor pressure metering motor 56 and responds to signals received from Reid vapor pressure analyzer 64. The computer has, before the dispensing begins, been inputted with information from the bar code on the vehicle and, optionally, with information from price input 82 and octane input pad 84. During and after dispensing until the next sale commences, the computer displays appropriate data on octane 92, price display 94, gallon/liter delivered display 96, and total sale display 98.

The customer sees little of this complexity but instead merely inputs (by hand or through the bar codes discussed above) the desired octane, Reid vapor pressure (if it is desired to have the customer input that information), and sees the appropriate price displayed. The customer then opens nozzle and dispensing valve 104 and receives fuel of the desired octane, etc., with the usual gallons/liters dispensed and total sale information being displayed continuously during the dispensing. Appropriate inputting of customer credit cards, account numbers, cash or credit indications, vehicle numbers, can readily be provided for.

The inputting can be simplified, e.g. by providing means for inputting merely the make, model, engine, and year of the vehicle so that the computer itself determines the optimum fuel mix. Reference to documents made in the specification is intended to result in such patents or literature being expressly incorporated herein by reference, including any patents or other literature references cited within such documents.

What is claimed:

1. An apparatus for blending and dispensing customized fuel to a vehicle in response to a bar Code on the vehicle comprising:
    a. multiple fuel component storage means connective with individual conduit means,
    b. a mixing means, for blending said fuel, fluidly connective with said storage means, and producing a blended or customized fuel,
    c. at least one analyzing means operatively associated with at least one individual fuel component, said mixing means or said blended fuel,
    d. a fuel dispensing means comprising a bar code reader fluidly connective with said mixing means
    e. a bar code on said vehicle,
    f. one or more computer means, receiving inputs from said bar code reader on said fuel dispensing means, for determining the fuel requirements of said vehicle based upon said bar code on said vehicle and for controlling the blending of fuel to produce said blended fuel required by, or specified for, said vehicle based upon said bar code on said vehicle, and g. a display means displaying at least one of cost, volume or properties of said customized fuel delivered to said vehicle in response to said bar code on said vehicle.

2. The apparatus of claim 1 wherein said multiple fuel component storage means comprise storage means for at least one of the following gasoline blending components:

a regular gasoline component, and alkylate component, a high Reid vapor pressure (RVP) component, and an alcohol component.

3. The apparatus of claim 1 wherein a single computer system receives input from said bar code on said vehicle and from said analyzing means and controls said blending in response thereto.

4. The apparatus of claim 1 wherein one fuel component is a replenishable fuel component.

5. The apparatus of claim 4 wherein said replenishable fuel component is methanol or ethanol.

* * * * *